US009498582B2

(12) United States Patent
Fuke et al.

(10) Patent No.: US 9,498,582 B2
(45) Date of Patent: Nov. 22, 2016

(54) LIQUID ADMINISTRATION DEVICE

(71) Applicant: Terumo Kabushiki Kaisha, Tokyo (JP)

(72) Inventors: Shigeaki Fuke, Kanagawa (JP);
Masaomi Imai, Kanagawa (JP);
Manabu Arinobe, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/596,014

(22) Filed: Jan. 13, 2015

(65) Prior Publication Data

US 2015/0126925 A1   May 7, 2015

Related U.S. Application Data

(63) Continuation of application No. PCT/JP2012/068595, filed on Jul. 23, 2012.

(51) Int. Cl.
*A61M 5/32* (2006.01)
*A61M 5/28* (2006.01)

(52) U.S. Cl.
CPC ........... *A61M 5/3271* (2013.01); *A61M 5/288* (2013.01); *A61M 5/326* (2013.01); *A61M 2005/3267* (2013.01)

(58) Field of Classification Search
CPC ............. A61M 5/288; A61M 5/3202; A61M 5/3243; A61M 5/3257; A61M 5/3271; A61M 5/3272; A61M 5/326; A61M 5/2033; A61M 2005/3247; A61M 2005/2013; A61M 2005/206; A61M 25/0631
See application file for complete search history.

(56) References Cited

U.S. PATENT DOCUMENTS

| 6,743,203 B1 | 6/2004 | Pickhard | |
| 2005/0273061 A1* | 12/2005 | Hommann | A61M 5/2033 604/198 |
| 2010/0168678 A1* | 7/2010 | Glocker | A61M 5/24 604/200 |
| 2011/0152822 A1* | 6/2011 | Drunk | A61J 1/065 604/415 |
| 2012/0101475 A1* | 4/2012 | Wilmot | A61M 5/2033 604/506 |
| 2013/0023825 A1* | 1/2013 | Edwards | A61M 5/2033 604/143 |

FOREIGN PATENT DOCUMENTS

| JP | 2001-521792 A | 11/2001 |
| JP | 2003-505159 A | 2/2003 |
| JP | 2005-319118 A | 11/2005 |
| WO | WO-99/22790 A1 | 5/1999 |

OTHER PUBLICATIONS

International Search Report dated Sep. 18, 2012 issued in Application No. PCT/JP2012/068595.

* cited by examiner

*Primary Examiner* — Imani Hayman
*Assistant Examiner* — James D Ponton
(74) *Attorney, Agent, or Firm* — Foley & Lardner LLP (57) ABSTRACT

A liquid administration device includes: a cylindrical body filled with liquid; a needle tube configured to communicate or be communicable with the cylindrical body at its tip side, and to have a sharp needle tip; a gasket configured to slide within the cylindrical body; an operation member configured to to discharge the liquid by pressing the gasket toward the tip direction; a cover member configured to be capable of moving to a first position, in which at least the needle tip is covered, to a second position, in which the needle tip is exposed, and to a third position, in which at least the needle tip is re-covered; and a cover member that can move from the first position to the second position to a third position to re-cover the needle tip.

17 Claims, 8 Drawing Sheets

LIQUID ADMINISTRATION DEVICE

CROSS-REFERENCE TO RELATED APPLICATIONS

This application is a continuation application filed under 35 U.S.C. 111(a) claiming benefit under 35 U.S.C. §§120 and 365(c) of PCT International Application No. PCT/JP2012/068595 filed on Jul. 23, 2012, the contents of which is hereby incorporated by reference in its entirety.

BACKGROUND

Technical Field

The present invention relates to a liquid administration device that can help increase safety after its use.

Background Art

Prefilled syringes, which are at least partially filled with a liquid preparation in an aseptic manner and capable of administering the liquid product have been known (see JP 2005-319118 A). The prefilled syringe disclosed in JP 2005-319118 A includes a syringe outer cylinder, a gasket, the liquid preparation, and a plunger. The syringe outer cylinder has an opening part from which the liquid preparation discharges. The gasket can slide within the syringe outer cylinder. The space surrounded by the syringe outer cylinder and the gasket is filled with the liquid preparation. The plunger is coupled to the base end side of the gasket and discharges the liquid preparation from the opening part by pressing the gasket toward the tip direction. In this prefilled syringe, the opening part of the syringe outer cylinder is sealed liquid-tightly with a cap in an unused state.

When the liquid preparation is administered using the prefilled syringe, first, the cap is removed from the opening part of the syringe outer cylinder, and then, an injection needle is mounted on the opening part from which the cap is removed. Next, a living body is punctured with the injection needle, and pressing operation by the plunger is performed in this punctured state. As a result, the liquid preparation is discharged from the opening part by the gasket, thus, the liquid preparation can be administered to the living body though the injection needle. After administration, that is, after use, the prefilled syringe is disposed. In disposing this after use, the prefilled syringe is sometimes disposed while the injection needle is still mounted. In this case, there may have been a problem with erroneous puncturing by the injection needle.

SUMMARY OF INVENTION

One objective of certain embodiments of the present invention is to provide a liquid administration device which can help to increase its safety after use.

Such an object is achieved by certain embodiments of the present invention as presented in descriptions (1) to (8) described below.

(1) A liquid administration device including:
a cylindrically-shaped cylindrical body configured to be at least partially filled with liquid in its inside;
a needle tube configured to be provided being communicated or communicable with the cylindrical body at the tip side of the cylindrical body, and to have a sharp needle tip at the tip;
a gasket configured to be capable of sliding within the cylindrical body;
an operation member configured to be provided at the base end side of the gasket and to perform pressing operation to discharge the liquid from the needle tube by pressing the gasket toward the tip direction;
a cover member configured to be capable of moving to a first position, in which at least the needle tip of the needle tube is covered, to a second position, moved from the first position to the base end direction, in which the needle tip is exposed, and to a third position, moved from the second position to the tip direction, in which at least the needle tip is re-covered; and
a restricting member configured to take a state where the cover member is allowed to move from the first position to the second position, and to take a state where moving back of the cover member to the second position is restricted after the cover member has moved from the second position to the third position.

(2) A liquid administration device including:
a cylindrically-shaped cylindrical body configured to be at least partially filled with liquid in its inside;
a needle tube configured to be provided being communicated or communicable with the cylindrical body at the tip side of the cylindrical body, and to have a sharp needle tip at the tip;
a gasket configured to be capable of sliding within the cylindrical body;
an operation member configured to be provided at the base end side of the gasket and to perform pressing operation to discharge the liquid from the needle tube by pressing the gasket toward the tip direction;
a cover member configured to be capable of moving to a first position, in which at least the needle tip of the needle tube is covered, to a second position, moved to the base end direction from the first position, in which the needle tip is exposed, and to a third position, moved to the tip direction from the second position, in which at least the needle tip is re-covered; and
a restricting member configured to be capable of restricting movement of the cover member,
wherein the restricting member is provided with a first engagement part and a second engagement part at different positions from each other,
the cover member is provided with a first cover side engagement part capable of being engaged with the first engagement part, and a second cover side engagement part capable of being engaged with the first engagement part at the base end side compared with the first cover side engagement part, at timing different from the first cover side engagement part,
the operation member is provided with an operation part side engagement part capable of being engaged with the second engagement part,
when the cover member is in the first position, the restricting member is made in a first state where the first engagement part is engaged with the first cover side engagement part,
when the cover member moves from the first position to the second position and the pressing operation by the operation member is complete, the restricting member moves together with the cover member, while the first engagement part is being engaged with the first cover side engagement part, and is made in a second state where the second engagement part is engaged with the operation part side engagement part, and
when the cover member moves from the second position to the third position, the first engagement part is removed from the first cover side engagement part and is engaged with the second cover side engagement part, while the second engagement part is being engaged with the operation part side engagement part, and thus the restricting member is made in a third state where moving back of the cover member to the second position is restricted.

(3) The liquid administration device described in the above (2), wherein the operation member is cylindrically-shaped and the outer peripheral part of the operation member has a holding part, which is held when the pressing operation is performed, each of the cover member and the restricting member is configured by a cylindrically-shaped member, and the cover member, the restricting member, and the holding part are arranged concentrically from inside in order.

(4) The liquid administration device described in the above (3), wherein relative rotation among the cover member, the restricting member, and the holding part is restricted.

(5) The liquid administration device described in any one of the above (2) to (4), wherein the first engagement part and the second engagement part are arranged in different positions along a center axis of the restricting member and also around the center axis of the restricting member.

(6) The liquid administration device described in any one of the above (2) to (5), wherein each of the first engagement part and the second engagement part deforms elastically.

(7) The liquid administration device described in any one of the above (1) to (6), including:

a support member configured to movably support the needle tube relative to the cylindrical body along its center axis direction, wherein the cylindrical body is bottomed cylindrically-shaped, and has a cylinder main body having an opening part at its bottom through which the liquid passes, and a sealing part configured by an elastic material that seals the opening part liquid-tightly, the needle tube is configured by a double ended needle further having a sharp base end side needle tip at the base end and is communicated with the cylindrical body by piercing the sealing part with the base end side needle tip, when the cover member is in the first position, the base end side needle tip is separated from the sealing part, and when the cover member moves to the second position, the cover member moves the needle tube with the support member toward the base end direction and the sealing part is pierced.

(8) The liquid administration device described in any one of the above (1) to (7) including a biasing member configured to bias the cover member toward the tip direction.

In addition, in the liquid administration device of certain embodiments of the present invention, it can be preferable that the first engagement part is provided at the inner peripheral part of the restricting member and has a first protruded part which protrudes toward inside, and the second engagement part is provided at the outer peripheral part of the restricting member and has a second protruded part which protrudes toward outside.

In addition, in the liquid administration device of certain embodiments of the present invention, it can be preferable that an inclined part, which is inclined relative to the center axis of the restricting member, is formed at the base end in each of the first protruded part and the second protruded part.

In addition, in the liquid administration device of certain embodiments of the present invention, it is preferable that each of the first cover side engagement part and the second cover side engagement part is configured by a recessed part provided at the outer peripheral part of the cover member.

In addition, in the liquid administration device of certain embodiments of the present invention, it is preferable that the operation part side engagement part is configured by a recessed part provided at the inner peripheral part of the holding part.

According to certain embodiments of the present invention, the restricting member can restrict the movement of the cover member in the third position, when the cover member moves to the third position. As a result, the needle tip of the needle tube can be better able to be covered by the cover member in the third position. As a result, the incidence of erroneous puncturing by the needle tip can be lowered after use of the liquid administration device, which can better ensure safety.

DETAILED DESCRIPTION

Hereinafter, a preferred embodiment of the liquid administration device of the present invention will be described in detail with reference to the attached drawings.

Figure 1:
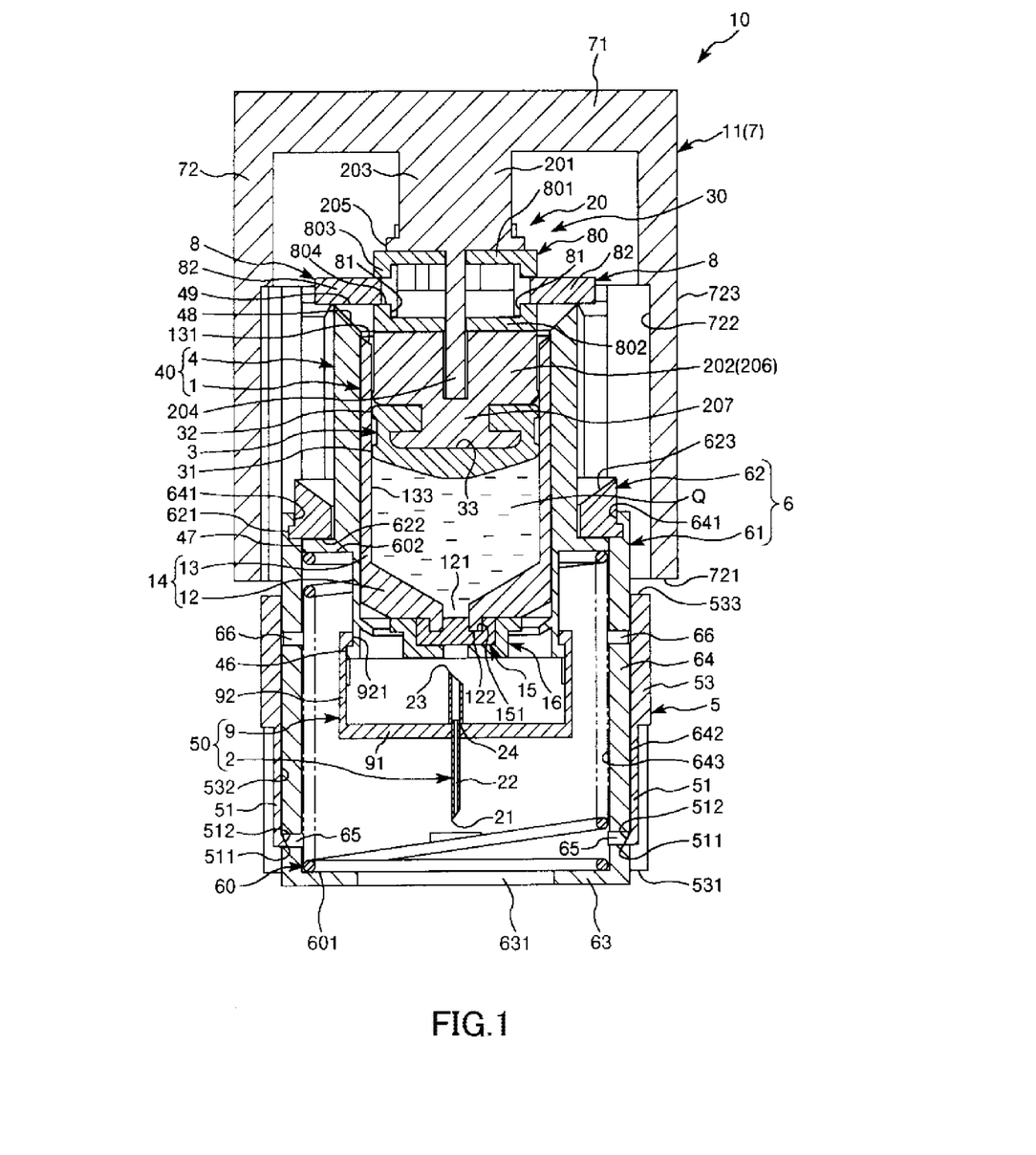
FIG. 1 is a longitudinal sectional view showing the operation state in use of a liquid administration device of an embodiment of the present invention.
Figure 2:
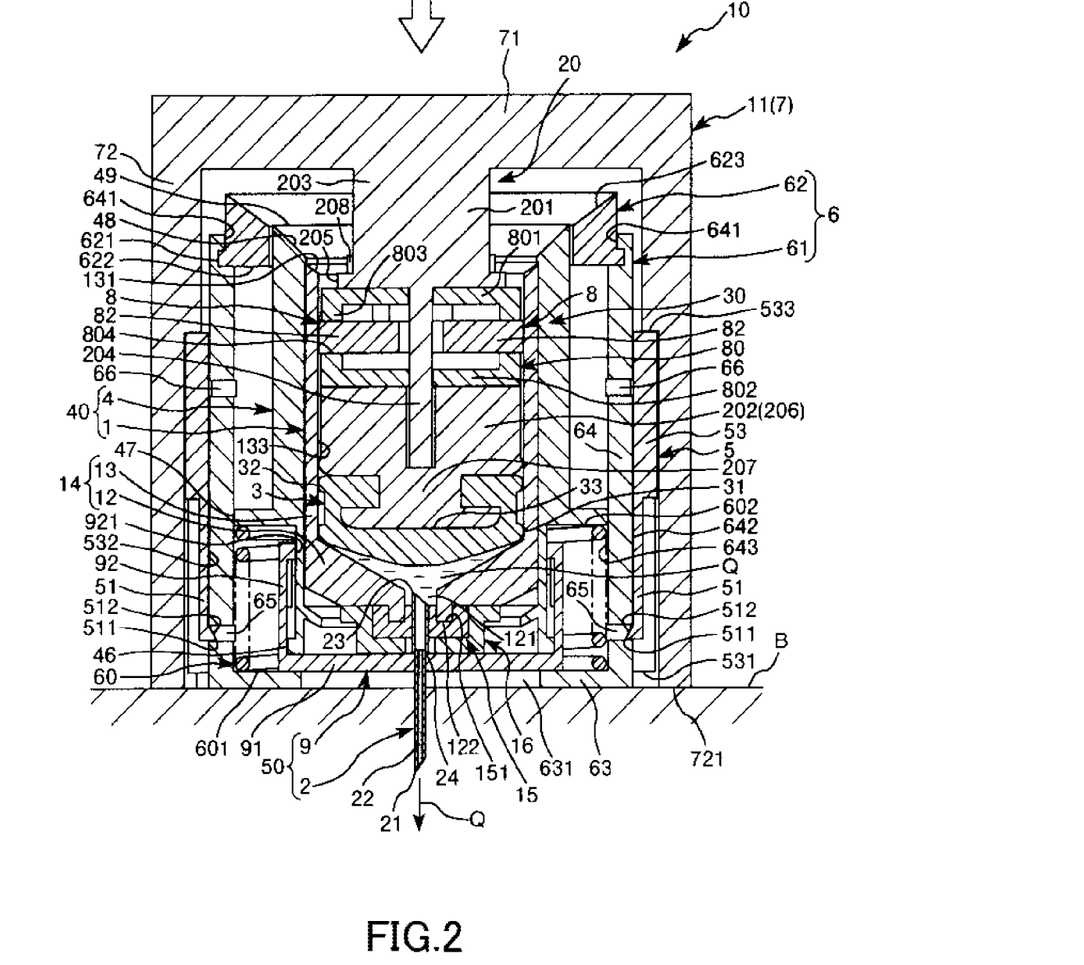
FIG. 2 is a longitudinal sectional view showing the operation state in use of the liquid administration device of an embodiment of the present invention.
Figure 3:
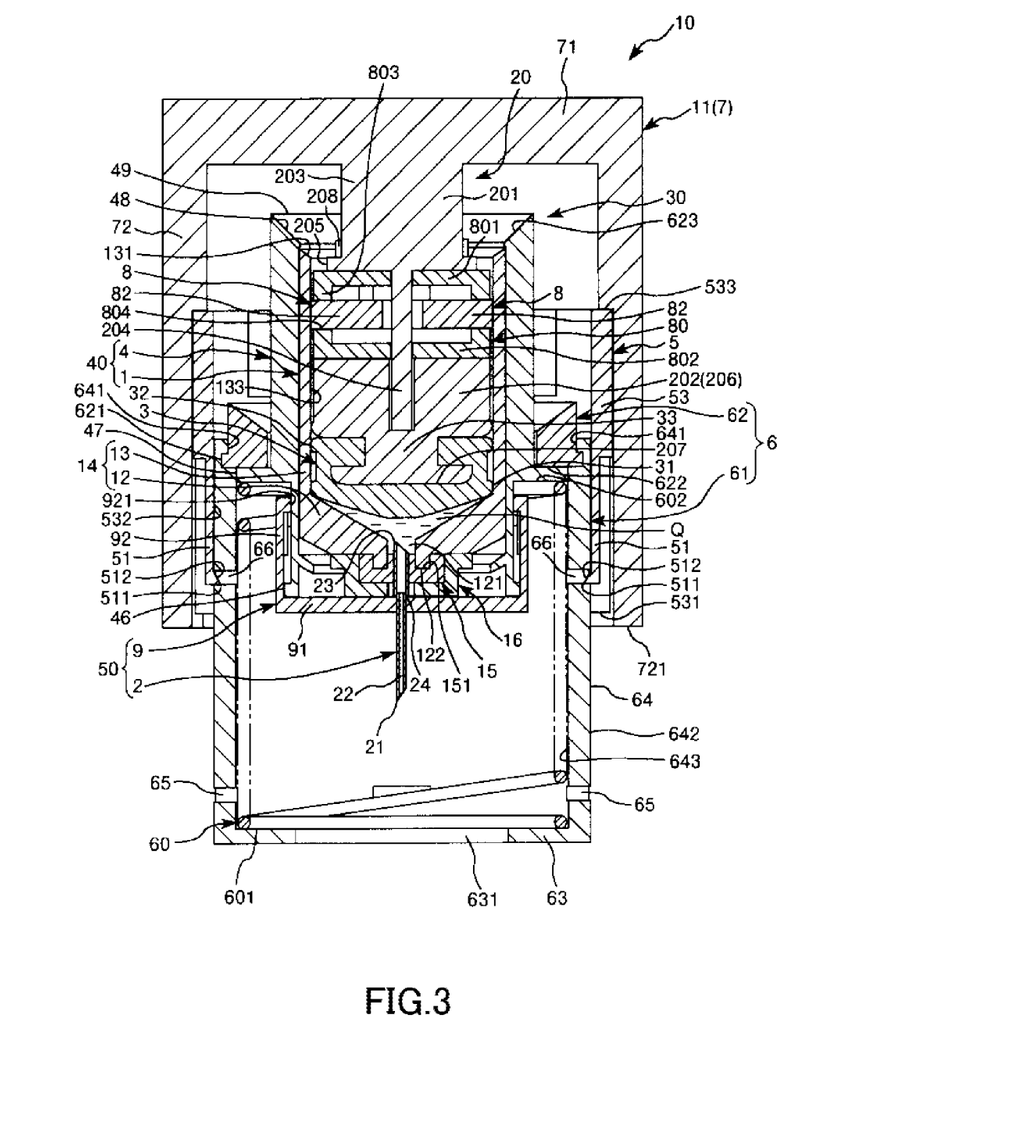
FIG. 3 is a longitudinal sectional view showing the operation state in use of the liquid administration device of the present invention.
Figure 4:
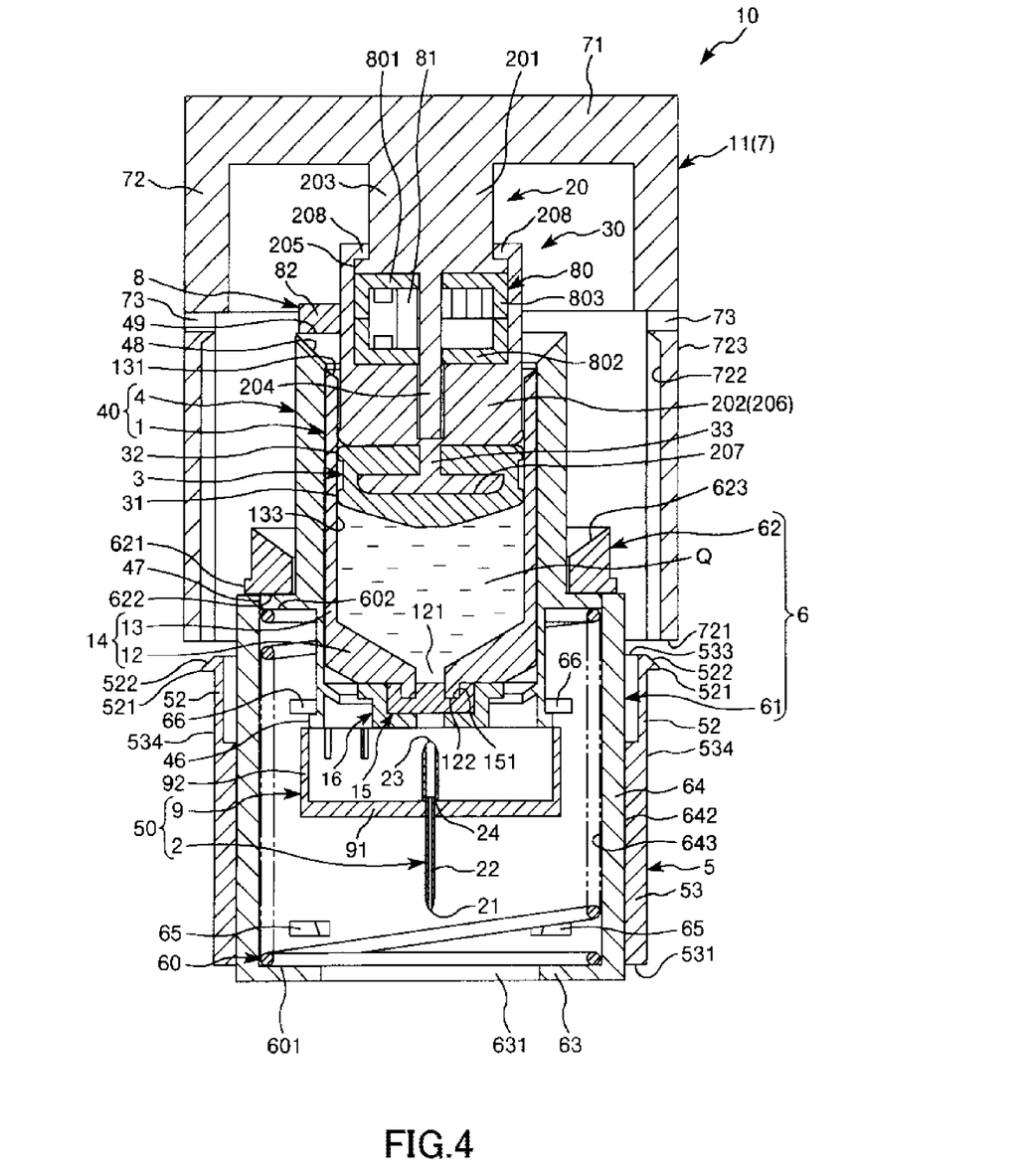
FIG. 4 is a longitudinal sectional view of the embodiment of the liquid administration device in the state shown in FIG. 1, when seen by changing an angle by 90 degrees around its axis.
Figure 5:
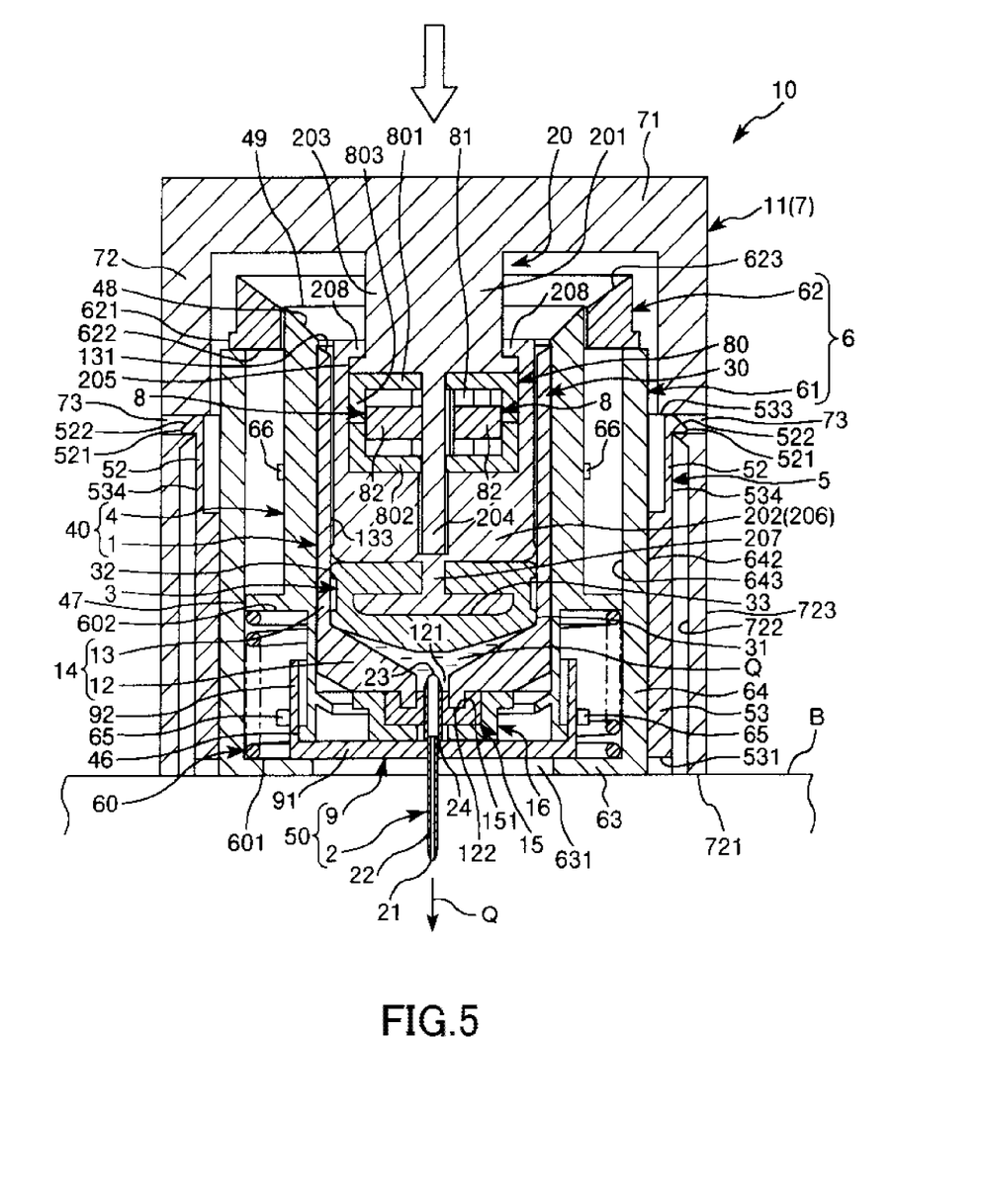
FIG. 5 is a longitudinal sectional view of the embodiment of the liquid administration device in the state shown in FIG. 2, when seen by changing the angle by 90 degrees around its axis.
Figure 6:
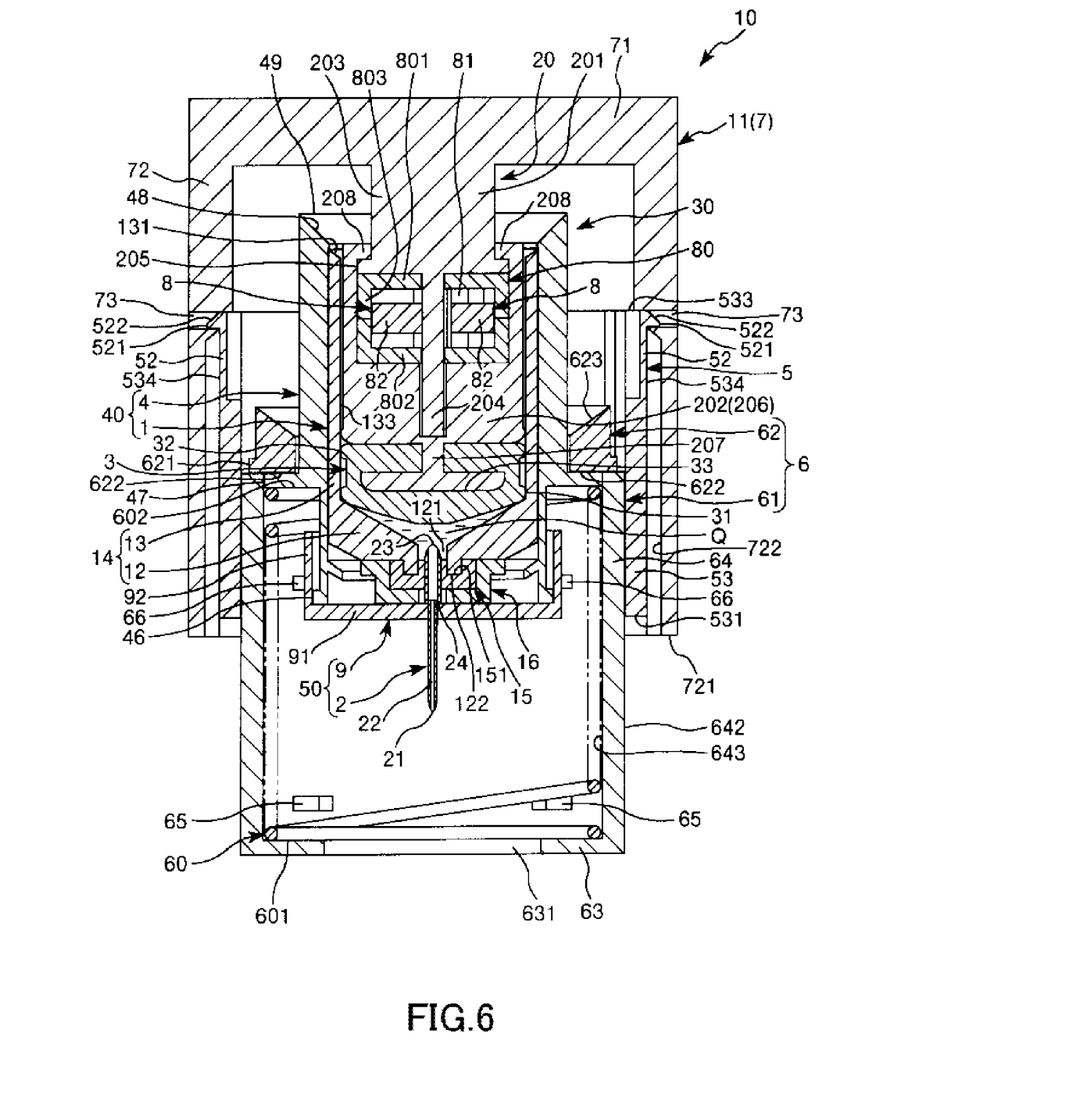
FIG. 6 is a longitudinal sectional view of the embodiment of the liquid administration device in the state shown in FIG. 3, when seen by changing the angle by 90 degrees around its axis.
Figure 7:
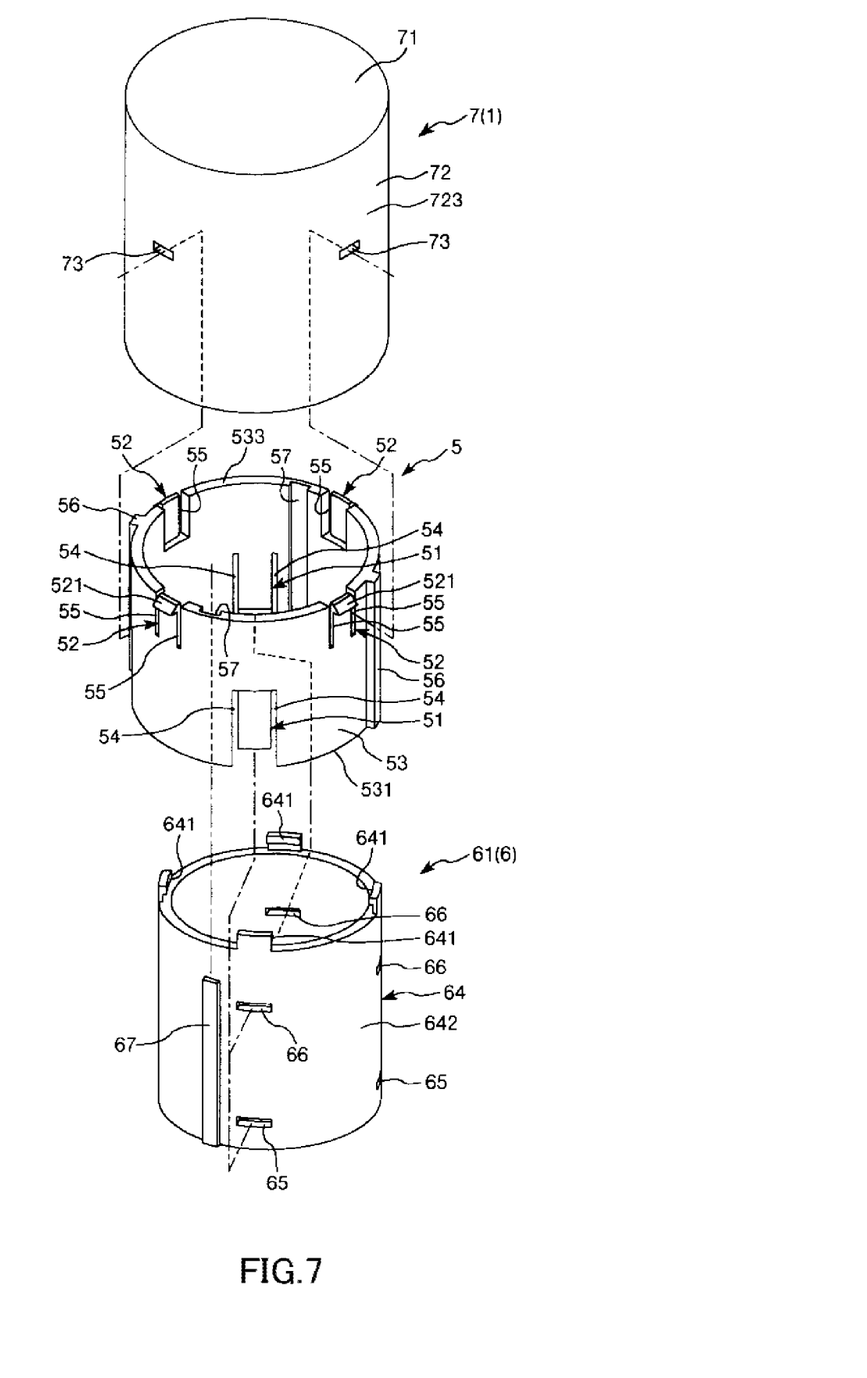
FIG. 7 is an exploded perspective view showing a positional relation among an operation member, a cover member, and a restricting member included in the liquid administration device of an embodiment of the present invention.
Figure 8:
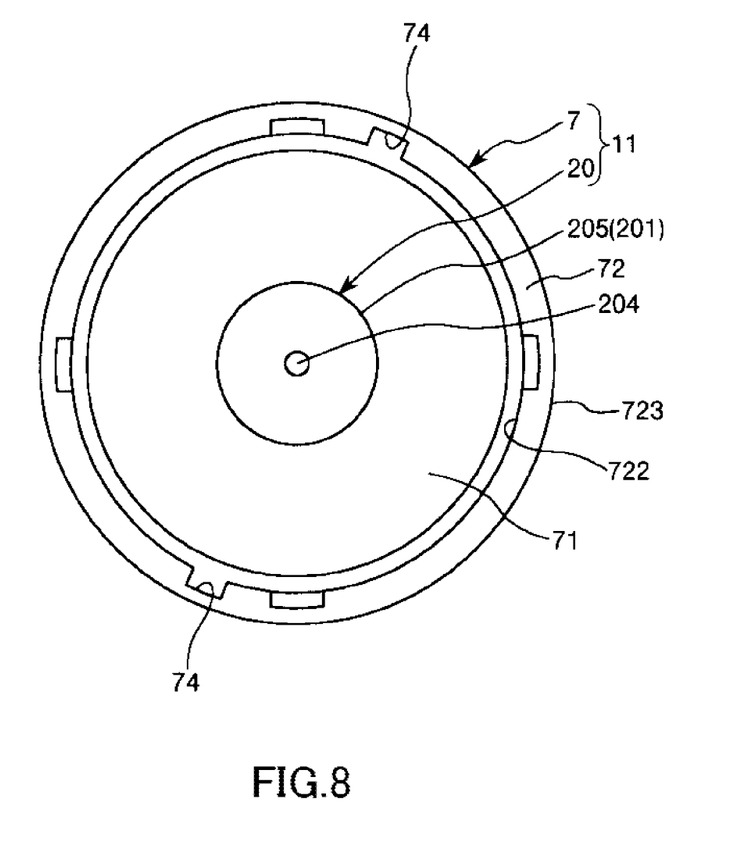
FIG. 8 is a view of the operation member shown in FIG. 7, seen from the tip side.

Each of FIGS. 1 to 3 is a longitudinal sectional view showing the operation state in use of a liquid administration device of the embodiment of the present invention. Each of FIGS. 4 to 6 is a longitudinal sectional view of the same liquid administration device in the state shown in FIGS. 1 to 3, when seen by changing an angle by 90 degrees around its axis. FIG. 7 is an exploded perspective view showing a positional relation among an operation member, a cover member, and a restricting member included in the liquid administration device of the present invention. FIG. 8 is a view of the operation member shown in FIG. 7, seen from the tip side. Hereinafter, for convenience of explanation, the upper side is referred to as "base end" or "upper (upper side)" and the lower side is referred to as "tip" or "lower (lower side) in FIGS. 1 to 7. The upper side is also referred to as the proximal side (that is, the side farther from the patient during use), while the lower side is referred to as the distal side (that is, the side closer to the patient during use).

The liquid administration device 10 shown in FIGS. 1 to 6 is a medical device used when liquid Q is administered (injected) into a living body B. The liquid Q is suitably selected according to its purpose of use. As the liquid Q, for example, medicinal liquids, mainly injected hypodermically, such as hematopoietic agent, vaccines, hormone preparations, antirheumatics, carcinostatic agents, anesthetics, and anticoagulants are raised.

The liquid administration device 10 includes a cylindrical body 40, a puncture needle 50, a gasket 3, an operation member 11, a restricting part for restricting the operation member (hereinafter simply referred to as "restricting part") 30, a cover member 6, a restricting member for restricting the cover member (hereinafter simply referred to as "restricting member") 5, and a coil spring 60 as a biasing member. The cylindrical body 40 includes an inner cylinder 1 and an outer cylinder 4. The puncture needle 50 includes a double ended needle 2 and a support member 9. The gasket 3 can slide within the inner cylinder 1 (cylindrical body 40). The operation member 11 is arranged at (coupled to) the base end side of the gasket 3. The restricting part 30 can restrict operation of the operation member 11. The cover member 6 is arranged at the outer peripheral side of the outer cylinder 4 (cylindrical body 40). The restricting member 5 can restrict movement of the cover member 6. The coil spring 60 biases the cover member 6.

As shown in FIGS. 1 to 6, the inner cylinder 1 has an inner cylinder body 14, which is a member including a bottom part 12 at the tip and a side wall 13 erected from the edge of the bottom part 12, that is, a member with a bottomed cylindrical shape. Then, inside of the inner cylinder 1 can be at least partially filled with the liquid Q. The bottom part 12 has a mortar shape. An opening part 121, through which the liquid Q passes, is formed at center of the bottom part 12.

The side wall 13 has a cylindrical shape. At the inner peripheral part of the base end of the side wall 13, an inner cylinder side tapered part 131 is formed. The inner diameter of the inner cylinder side tapered part 131 is gradually reduced toward the tip direction.

In addition, the inner cylinder 1 has a sealing member (sealing part) 15, which seals the opening part 121 of the inner cylinder body 14 liquid-tightly, and a fixing member 16, which fixes the sealing member 15 from its tip side.

The sealing member 15 is a disk-shaped elastic piece, and a ring-shaped recessed part 151 is formed on its base end surface. A ring-shaped protruded part 122, which is formed protrudedly on the opening part 121 of the inner cylinder body 14, can fit liquid-tightly to this recessed part 151. As a result, the sealing member 15 is attached to the opening part 121 of the inner cylinder body 14 and can seal the opening part 121 liquid-tightly.

The fixing member 16 is a ring-shaped member. Then, this fixing member 16 fits to the sealing member 15 from its outer peripheral side, and holds the sealing member 15 between the fixing member 16 and the protruded part 122. Thus, the sealing member 15 can be fixed to the inner cylinder body 14. As a result, removal of the sealing member 15 from the inner cylinder body 14 is better able to be prevented.

In addition, a constituent material for the inner cylinder body 14, the fixing member 16, the outer cylinder 4, the restricting member 5, the cover member 6, the support member 9, and the operation member 11 are not particularly limited. Examples include various types of resins such as polyvinyl chloride, polyethylene, polypropylene, cyclic polyolefins, polystyrene, poly(4-methylpentene-1), polycarbonates, acrylic resins, acryl nitrile-butadiene-styrene copolymer, polyesters such as polyethylene terephthalate and polyethylene naphthalate, butadiene-styrene copolymer, and polyamides (e.g. nylon 6, nylon 6-6, nylon 6-10 and nylon 12). Of these, it is preferred to use resins such as polypropylene, cyclic polyolefins, polyesters and poly-(4-methylpentene-1) in view of the ease in molding.

In addition, an elastic material included in the sealing member 15 and the gasket 3 is not particularly limited. Examples include various rubber materials such as natural rubber, butyl rubber, isoprene rubber, butadiene rubber, styrene-butadiene rubber, silicone rubber, various types of thermoplastic elastomers, such as polyurethane, polyester, polyamide, olefin, and styrene elastomers, or elastic materials such as mixtures thereof.

At the outer peripheral side of the inner cylinder 1, the outer cylinder 4 is arranged concentrically with the inner cylinder 1. The outer cylinder 4 is a cylindrically-shaped member and each of both ends thereof is opened. The length of the outer cylinder 4 is longer than that of the inner cylinder 1. Then, the inner cylinder 1 is fixed to (coupled to) inside of this outer cylinder 4.

At the outer peripheral part of the outer cylinder 4, a first flange part 46 and a second flange part 47 are protrudedly formed. The first flange part 46 is formed to be ring-shaped at the tip of the outer cylinder 4 along its circumferential direction. The second flange part 47 is formed to be ring-shaped in midway in the longitudinal direction of the outer cylinder 4 along its circumferential direction. The outer diameter of this second flange part 47 is larger than the outer diameter of the first flange part 46.

At the inner peripheral part of the base end of the outer cylinder 4, an outer cylinder side tapered part 48 is formed. The inner diameter of the outer cylinder side tapered part 48 is gradually reduced toward the tip direction. A taper angle of the outer cylinder side tapered part 48 is the same as the taper angle of the inner cylinder side tapered part 131 of the inner cylinder 1. In addition, the outer cylinder side tapered part 48 is positioned at the base end side compared with the inner cylinder side tapered part 131, and includes an inclined surface continued to the inner cylinder side tapered part 131. That is, the outer cylinder side tapered part 48 is positioned on the same inclined surface as the inner cylinder side tapered part 131.

The puncture needle 50 is arranged at the tip side of the cylindrical body 40. The puncture needle 50 includes the double ended needle 2 and the support member 9.

The double ended needle 2 is a hollow needle tube, which has a sharp tip side needle tip (needle tip) 21 at the tip and a sharp base end side needle tip 23 also at the base end. In this double ended needle 2, the living body B can be punctured with the tip side needle tip 21 and the sealing member 15 of the inner cylinder 1 can be pierced with the base end side needle tip 23. The double ended needle 2 is a different-diameter needle, in which the part at the tip side needle tip 21 side and the part at the base end side needle tip 23 side have different outer diameters. In the present embodiment being discussed, the part at the tip side needle tip 21 side is thinner than the part at the base end side needle tip 23 side.

A lumen part (hollow part) of the double ended needle 2 is communicating with the inner cylinder 1, in a state where the base end side needle tip 23 is piercing the sealing member 15 of the inner cylinder 1, and functions as a flow path 22, through which the liquid Q from the inner cylinder 1 passes. Then, the liquid Q is injected into the living body B through the flow path 22, in a state where the living body B is punctured to a predetermined depth from the skin with the tip side needle tip 21.

A constituent material for the double ended needle 2 is not particularly limited, and for example, metallic materials such as stainless steel, aluminum or aluminum alloys, and titanium or titanium alloys are raised.

The double ended needle 2 with such a configuration is attached to the outer cylinder 4 (cylindrical body 40) through the support member 9. The support member 9 movably supports the double ended needle 2 relative to the outer cylinder 4 along its center axis direction. This support member 9 includes a disk-shaped fixing part (support part) 91 and a wall part 92 erected toward the base end direction from the edge of the fixing part 91.

The fixing part 91 can support and fix the double ended needle 2 at its center. The part supported by the fixing part 91 of the double ended needle 2 is in midway in the longitudinal direction of the double ended needle 2, that is, near a step part 24 where the outer diameter of the double ended needle 2 is precipitously changed in the present embodiment being discussed.

The wall part 92 is a ring-shaped part along the edge of the fixing part 91, and is a part in which the inner diameter is substantially equal to or slightly larger than the diameter of the first flange part 46 of the outer cylinder 4. As shown in FIGS. 1 to 3, a plurality of engagement parts 921 is formed at the inner peripheral part of the base end of the wall part 92. The plurality of engagement parts 921 protrudes to inside and is engaged with the first flange part 46. Each of engagement parts 921 is arranged at equal intervals along the circumferential direction of the wall part 92. Then, each of engagement parts 921 is engaged with the first flange part 46, so that removal of the puncture needle 50 from the tip of the cylindrical body 40 is prevented.

As described above, the puncture needle 50 is movably supported relative to the outer cylinder 4 along its center axis direction through the support member 9. As a result, the puncture needle 50 can take a separated state where the base end side needle tip 23 is separated from the sealing member 15 of the cylindrical body 40 as shown in FIGS. 1 and 4, and a pierced state where the base end side needle tip 23 pierces the sealing member 15 as shown in FIGS. 2, 3, 5 and 6. Therefore, unintentional leaking of the liquid Q from the double ended needle 2 is prevented until the pierced state is realized.

The cover member 6 is arranged at the outer peripheral side of the cylindrical body 40 and is movably supported relative to the outer cylinder 4 (cylindrical body 40) along its axis direction as with the puncture needle 50. As a result, the cover member 6 can move to a first position (see FIGS. 1, and 4), a second position (see FIGS. 2 and 5), and a third position (see FIGS. 3 and 6).

The first position is the position in which the cover member 6 covers at least the tip side needle tip 21 of the double ended needle 2. The cover member 6 is positioned in the first position, so that erroneous puncturing by the tip side needle tip 21, or damage to the tip side needle tip 21 can be better able to be prevented.

The second position is the position, in which the cover member 6 moves (retreats) from the first position to the base end direction and thus the tip side needle tip 21 is exposed. The cover member 6 is positioned in the second position, so that the living body B can be punctured with the tip side needle tip 21 before use of the liquid administration device 10.

The third position is the position, in which the cover member 6 moves from the second position to the tip direction and re-covers at least the tip side needle tip 21. The cover member 6 is positioned in the third position, so that erroneous puncturing by the tip side needle tip 21 can be better attempted to be prevented after use of the liquid administration device 10.

The above-described puncture needle 50 is in the separated state when the cover member 6 is in the first position. When the cover member 6 moves to the second position, the cover member 6 presses and moves the puncture needle 50 (double ended needle 2 with the support member 9) toward the base end direction, and makes the puncture needle 50 in the pierced state.

The cover member 6 is an assembly, which is made by assembling and fixing two components to each other. In the present embodiment being discussed, the cover member 6 includes a cylindrically-shaped cover member body 61 and a ring-shaped ring member 62, which are configured separately with each other. The ring member 62 is arranged inside of the cover member body 61 concentrically with the cover member body 61.

The cover member body 61 includes a plate-like tip wall part (bottom part) 63 at the tip and a side wall 64 erected from the edge of the tip wall part 63. That is, the cover member body 61 is configured by a member with a bottomed cylindrical shape.

At the center of the tip wall part 63, an opening part 631, which penetrates the center, is formed As shown in FIGS. 2 and 5, when the cover member 6 is in the second position, the tip side needle tip 21 of the puncture needle 50 is protruded (exposed) from the opening part 631.

The side wall 64 has a cylindrical shape. As shown in FIG. 7, a plurality (four in the configuration shown in FIG. 7) of engagement parts 641, which protrudes toward inside, is formed at the inner peripheral part of the base end of the side wall 64. Each of engagement parts 641 is arranged at equal intervals along the circumferential direction of the side wall 64.

A flange part 621 is protrudedly formed at the outer peripheral part of the ring member 62. This flange part 621 is engaged with each of engagement parts 641 of the cover member body 61, so that the ring member 62 is fixed relative to the cover member body 61 (see FIGS. 1 to 3).

In addition, as shown in FIGS. 1, 3, 4, and 6, when the cover member 6 is in the first position or in the third position, the second flange part 47 of the outer cylinder 4 is engaged with a tip surface 622 of the ring member 62 from its tip side. With this engagement, removal of the cover member 6 from the outer cylinder 4 is prevented.

In addition, at the inner peripheral part of the base end of the ring member 62, a restriction release part 623 configured by the tapered part is provided. The inner diameter of the restriction release part 623 is gradually reduced toward the tip direction. This restriction release part 623 is a part which releases the restriction of the restricting part 30 relative to the operation member 11.

The coil spring 60 is stored in a compressed state inside the cover member body 61. In this coil spring 60, its tip 601 abuts on the tip wall part 63 of the cover member body 61, and a base end 602 abuts on the second flange part 47 of the outer cylinder 4. Then, the coil spring 60 is compressed between them. As a result, the cover member 6 can be biased to the direction from the second position to the first position (third position), that is, to the tip direction. By such biasing force of the coil spring 60, the tip side needle tip 21 can be covered with the cover member 6 before/after use of the liquid administration device 10. Thus, erroneous puncturing by the tip side needle tip 21 can be better attempted to be prevented.

A constituent material of the coil spring 60 is not particularly limited. For example, the metallic material such as stainless steel can be used.

The gasket 3 is slidably stored along the axis direction of the inner cylinder 1. The space, surrounded by this gasket 3 and the inner cylinder 1, is preliminarily filled with the liquid Q. Then, as shown in FIGS. 2 and 5, the gasket 3 moves toward the tip direction, so that the liquid Q in the inner cylinder 1 can be pushed out from the double ended needle 2, which is communicating with the inner cylinder 1.

An outer shape of this gasket 3 is cylindrically-shaped, and two protruded parts 31 and 32 are protrudedly formed at its outer peripheral part. The protruded parts 31 and 32 are separated along the axis direction of the gasket 3. Each of protruded parts 31 and 32 is ring-shaped along the circumferential direction of the gasket 3, and the outer diameter thereof, in a natural state where external force is not given, is slightly larger than the inner diameter of the inner cylinder 1. As a result, each of protruded parts 31 and 32 can slide while closely in contact with an inner peripheral part 133 of the side wall 13 of the inner cylinder 1. Thus, it is possible to retain the liquid-tightness and improve slidability.

At a base end surface of the gasket 3, in which the recessed part 33 to be coupled is opened, a coupling part 207 of the operation member 11 is inserted (fitted).

The operation member 11 is a member, which functions as "a pusher (plunger)", to perform pressing operation (discharging operation) to discharge the liquid Q from the double ended needle 2 by pressing the gasket 3 toward the tip direction. The operation member 11 is arranged at the outer peripheral side of the cover member 6 and has an operation member body 7 and a coupling part 20.

The operation member body 7 is a cup-shaped member and includes a top board 71 and a wall part 72, which protrudes toward the tip direction from the edge of the top board 71.

The top board 71 is a disk-shaped part.

The wall part 72 is a cylindrically-shaped part formed along the edge of the top board 71. Then, the outer peripheral part of the wall part 72 functions as a holding part to be held when the pressing operation is performed.

In addition, as shown in FIGS. 1 and 4, the wall part 72 covers from the base end side to the base end of the cover member 6 in an unused state of the liquid administration device 10. As a result, the restricting part 30 arranged at the coupling part 20 described below can be prevented from being touched by a hand of a user (operator). Therefore, unintentional release of restriction relative to the operation member 11 of the restricting part 30 can be better able to be prevented.

The coupling part 20 is the part to be coupled to the gasket 3 and is formed protrudedly toward the tip direction at the center of the top board 71. This coupling part 20 is column-shaped as a whole and can be divided into a first part 201 at the base end side and a second part 202 at the tip side.

The first part 201 is integrally formed with the top board 71 and has a large-diameter part 203 and a small-diameter part 204. The outer diameter of the first part 201 is reduced in a stepwise manner toward the tip side. At a boundary part between the large-diameter part 203 and the small-diameter part 204, a flange part 205 is formed. The flange part 205 protrudes in a ring shape toward its circumferential direction.

The second part 202 is configured separately from the first part 201 and has a base part 206, the coupling part 207, and a plurality of (for example, four) engagement parts 208.

The base part 206 is a cylindrically-shaped part, into the center of which the small-diameter part 204 is inserted. Then, a housing 80 of the restricting part 30 described below can be held between this base part 206 and the flange part 205 of the first part 201.

At the tip surface of the base part 206, the coupling part 207, corresponding to the shape of the recessed part 33 of the gasket 3, is formed. This coupling part 207 is inserted into the recessed part 33 of the gasket 3, so that the operation member 11 and the gasket 3 are coupled.

At the base end surface of the base part 206, a plurality of engagement parts 208 is protruded toward the base end direction. These engagement parts 208 are arranged at equal intervals along the circumferential direction of the base part 206. The base end of each of engagement parts 208 is bent into a hook shape, and can be engaged with the flange part 205 of the first part 201. As a result, the state, in which the housing 80 of the restricting part 30 is held between the base part 206 and the flange part 205 of the first part 201, can be maintained. Therefore, the restricting part 30 is fixed relative to the operation member 11.

The restricting part 30 has a pair of restricting parts 8 and the housing 80, which stores each of restricting parts 8.

Each of restricting parts 8 is a member, which displaces between a restricting position (see FIGS. 1 and 4) for restricting the pressing operation of the operation member 11, and a releasing position (see FIGS. 2 and 5) for releasing the restriction of the pressing operation described above by retreating from the restricting position.

Each of restricting parts 8 is a small piece arranged about midway in the longitudinal direction of the small-diameter part 204 of the coupling part 20 of the operation member 11 through the small-diameter part 204. Then, one restricting part 8 can approach to or be separated from the other restricting part 8. These restricting parts 8 are separated from each other in the restricting position, and these restricting parts 8 approach each other in the releasing position compared with a separated state in the above-described restricting position.

In each of restricting parts 8 arranged in this manner, the part at the small-diameter part 204 side becomes an enlargement part 81, in which the width and the thickness are enlarged. The enlargement part 81 is engaged with the housing 80, so that the restricting part 8 is prevented from being removed from the housing 80 in the restricting position (for example, see FIG. 1).

The part at the opposite side to the enlargement part 81 of each of restricting parts 8, protrudes from the housing 80 in the restricting position, and becomes an engagement part 82 to be engaged with a base end 49 of the outer cylinder 4. By this engagement, the pressing operation by the operation member 11 is restricted. In the releasing position, the engagement between the engagement part 82 and the base end 49 of the outer cylinder 4 is released. By this release, the pressing operation by the operation member 11 is made possible. The movement of each of restricting parts 8 from the restricting position to the releasing position is made by the cover member 6 which has moved to the second position.

The coil spring (not shown), as a biasing part to bias each of restricting parts 8, is arranged in the compressed state between the restricting parts 8. As a result, each of restricting parts 8 can be biased to the direction toward the restricting position. As a result, each of restricting parts 8 can stay in the restricting position, and a restricted state relative to the operation member 11 can be better able to be maintained.

The housing 80 is a hollow body (box body), and can store each of restricting parts 8 and the coil spring in its hollow part. This housing 80 is held between the flange part 205 of the first part 201 of the operation member 11 and the base part 206 of the second part 202, and its holding state is maintained by the engagement part 208. As a result, the housing 80 (restricting part 30) is better fixed relative to the operation member 11.

In the housing 80, the small-diameter part 204 of the coupling part 20 of the operation member 11 is inserted from a top board 801 to a bottom board 802. In addition, at two parts via the small-diameter part 204 of a side wall 803 of the housing 80, an opening part 804, from which each of restricting parts 8 protrudes, is formed to be penetrated.

A constituent material of the restricting part 8 and the housing 80 is not particularly limited. For example, the constituent material similar to that of the inner cylinder body 14 can be used.

As shown in FIGS. 1 to 6, at the outer peripheral side of the cover member 6, the restricting member 5, configured by a member with a cylindrical shape, is arranged. As shown in FIG. 7, in the liquid administration device 10, the cover member 6, restricting member 5, and the wall part 72 of the operation member body 7 are arranged concentrically from inside in this order.

The restricting member 5 is movably provided relative to the cover member 6 along its axis direction. Then, according to the position of the restricting member 5 relative to the cover member 6, the movement of the cover member 6 from the first position to the second position (see FIGS. 1, 2, 4, and 5) can be allowed, or moving back of the cover member 6 to the second position can be restricted, after the cover member 6 has moved from the second position to the third position (see FIGS. 3 and 6).

As shown in FIGS. 1 to 3 and 7, the restricting member 5 has a plurality of (four in the present embodiment being discussed) first engagement parts 51. Each of the first engagement parts 51 is a part to be engaged with the cover member body 61 of the cover member 6. Although the number of installation of the first engagement parts 51 is four in the present embodiment, it is not limited thereto. For example, the number may be one, two, three, five or more.

In addition, as shown in FIGS. 4 to 7, the restricting member 5 has a plurality of (four in the present embodiment) second engagement parts 52 at a position different from each of first engagement parts 51. Each of second engagement parts 52 is the part to be engaged with the wall part 72 of the operation member body 7. Although the number of installation of the second engagement parts 52 is four in the present embodiment, it is not limited thereto. For example, the number may be one, two, three, five, or more.

Each of the first engagement parts 51 is arranged at equal intervals along the circumferential direction of the restricting member 5. Since the configuration of each of first engagement parts 51 is the same, hereinafter, one of the first engagement parts 51 will be described below as a representative.

As shown in FIG. 7, at a cylindrical wall (wall part) 53 of the cylindrically-shaped restricting member 5, two slits 54 are formed from a tip 531 of the cylindrical wall 53 to midway in the center axis direction. The first engagement part 51 is a small piece provided between the two slits 54. As a result, the first engagement part 51 becomes an elastic piece which deforms elastically.

As shown in FIGS. 1 to 3, at the tip of the first engagement part 51, a first protruded part 511 is formed protrudedly. This first protruded part 511 is the part, which protrudes toward inside from an inner peripheral part 532 being the part of the cylindrical wall 53 included in the first protruded part 511. As a result, at the first protruded part 511, the first engagement part 51 can be engaged with a first cover side engagement part 65 (see FIGS. 1 and 2) of the cover member 6 or a second cover side engagement part 66 (see FIG. 3) described below.

In addition, at the base end of the first protruded part 511, an inclined part 512 is formed. The inclined part 512 is inclined relative to the center axis of the cylindrical wall 53 (restricting member 5). Then, the first protruded part 511 engaged with the first cover side engagement part 65 of the cover member 6 can easily go beyond the first cover side engagement part 65 by the inclined part 512, when removed from the first cover side engagement part 65. As a result, the first protruded part 511 can be easily removed from the first cover side engagement part 65.

In addition, as described above, the first engagement part 51 can deform elastically. Then, the first protruded part 511 removed from the first cover side engagement part 65 can be engaged with the second cover side engagement part 66 by its own elastic force of the first engagement part 51, in a position to be engaged with the second cover side engagement part 66.

As shown in FIG. 7, each of the second engagement parts 52 can be arranged at equal intervals along the circumferential direction of the restricting member 5. As described above, although each of first engagement part 51 is also arranged at equal intervals along the circumferential direction of the restricting member 5, the first engagement part 51 and the second engagement part 52 are arranged in positions, for example, different by 90 degrees around the center axis of the restricting member 5.

Because the configuration of each of second engagement parts 52 is the same, hereinafter, one of the second engagement parts 52 will be described below as a representative example.

As shown in FIG. 7, at a cylindrical wall 53 of the restricting member 5, the two slits 55 are formed from a base end 533 of the cylindrical wall 53 to midway in the center axis direction. The second engagement part 52 is a small piece provided between the two slits 55. As a result, the second engagement part 52 becomes an elastic piece which deforms elastically.

As shown in FIGS. 4 to 7, at the base end of the second engagement part 52, a second protruded part 521 is formed. This second protruded part 521 is the part, which protrudes toward outside from an outer peripheral part 534 being the part of the cylindrical wall 53 included in the second protruded part 521. As a result, at the second protruded part 521, the second engagement part 52 can be engaged with an operation part side engagement part 73 of the operation member body 7 described below (see FIGS. 5 and 6)

In addition, at the base end of the second protruded part 521, an inclined part 522 is formed. The inclined part 522 is inclined relative to the center axis of the cylindrical wall 53. Then, when the second protruded part 521 is engaged with the operation part side engagement part, the second protruded part 521 can easily go beyond the part from the tip 721 of the operation member body 7 to the operation part side engagement part 73 by the inclined part 522. As a result, the second protruded part 521 can be easily engaged with the operation part side engagement part 73.

In addition, as described above, the second engagement part 52 can deform elastically. Then, the second protruded part 521, which has gone beyond the part from the tip 721 of the operation member body 7 to the operation part side engagement part 73, can be engaged with the operation part side engagement part 73 by its own elastic force of the second engagement part 52, in a position to be engaged with the operation part side engagement part 73.

As shown in FIGS. 1 to 3 and 7, the cover member body 61 of the cover member 6 has the plurality of (four in the present embodiment) first cover side engagement parts 65. Each of the first cover side engagement parts 65 is a part capable of being engaged with each of the first engagement parts 51 of the restricting member 5.

The cover member body 61 of the cover member 6 has a plurality of (four in the present embodiment) second cover side engagement parts 66 at the base end side compared with each of first cover side engagement parts 65. Each of the second cover side engagement parts 66 is apart capable of being engaged with each of first engagement parts 51 of the restricting member 5 at timing different from the first cover side engagement part 65.

Although the numbers of installation of the first cover side engagement part 65 and the second cover side engagement part 66 are four in the present embodiment, it is not limited thereto as long as the number is the same as the number of installations of the first engagement part 51.

Each of first cover side engagement parts 65 and each of second cover side engagement parts 66 can be arranged at equal intervals along the circumferential direction of the cover member body 61 (cover member 6). Among these engagement parts, one of first cover side engagement parts 65 and one of second cover side engagement parts 66 right above it form a couple. Then, one of first engagement parts 51 can be engaged with the engagement part which has become the couple at different times (see FIGS. 1 to 3).

Each of first cover side engagement parts 65 and each of second cover side engagement parts 66 are through holes (recessed parts), which are formed by penetrating from an outer peripheral part 642 of the cover member body 61 (side wall 64) through an inner peripheral part 643. As a result, the first protruded part 511 of the first engagement part 51 can be engaged with the first cover side engagement part 65 or the second cover side engagement part 66.

As shown in FIGS. 4 to 7, the operation member body 7 of the operation member 11 has a plurality of (four in the present embodiment) operation part side engagement parts 73. Each of operation part side engagement parts 73 is a part capable of being engaged with each of second engagement parts 52 of the restricting member 5. Although the number of installations of the operation part side engagement part 73 is four in the present embodiment, it is not limited thereto as long as the number is the same as the number of installations of the second engagement part 52.

Each of operation part side engagement parts 73 is arranged at equal intervals along the circumferential direction of the wall part 72 of the operation member body 7 (operation member 11).

In addition, each of operation part side engagement parts 73 is a through hole (recessed part), which is formed by penetrating from an inner peripheral part 722 of the wall part 72 through an outer peripheral part 723. As a result, the second protruded part 521 of the second engagement part 52 can be better able to be engaged with the operation part side engagement part 73.

Then, according to the position of the cover member 6, restricting member 5 can take a first state shown in FIGS. 1 and 4, a second state shown in FIGS. 2 and 5, and a third state shown in FIGS. 3 and 6.

The first state is the state where each of first engagement parts 51 (first protruded part 511) of the restricting member 5 is engaged with each of the first cover side engagement parts 65 of the cover member 6, when the cover member 6 is in the first position.

In the second state, the restricting member 5 moves with the cover member 6, while each of the first engagement parts 51 of the restricting member 5 is being engaged with each of first cover side engagement parts 65 of the cover member 6, when the cover member 6 moves from the first position to the second position and the pressing operation by the operation member 11 has been complete. Then, at the position to which they have moved, each of second engagement parts 52 (second protruded part 521) of the restricting member 5 is engaged with each of operation part side engagement parts 73 of the operation member 11.

In the third state, each of first engagement parts 51 of the restricting member 5 is removed from each of first cover side engagement parts 65 of the cover member 6 and is engaged with each of second cover side engagement parts 66 of the cover member 6, while each of second engagement parts 52 of the restricting member 5 is being engaged with each of operation part side engagement parts 73 of the operation member 11, when the cover member 6 moves from the second position to the third position. As a result, moving back of the cover member 6 to the second position is restricted.

The restricting member 5 can take such a first state, a second state, and a third state in order. The details of this will be described with the usage of the liquid administration device 10 and the operation state when in use described below.

In the liquid administration device 10, the cover member 6, the restricting member 5, and the operation member body 7 (wall part 72) of the operation member 11 are configured, so that relative rotation around the center axis of the liquid administration device 10 is restricted. As a result, each of first engagement parts 51 of the restricting member 5 can be better able to be engaged in order with the first cover side engagement part 65 and the second cover side engagement part 66 of the cover member 6 corresponding to the first engagement part 51. In addition, each of second engagement parts 52 of the restricting member 5 can be better able to be engaged with the operation part side engagement part 73 of the operation member 11 corresponding to the second engagement part 52. Then, by each of such engagements, the restricting member 5 can be better able to take each state of the first state, the second state, and the third state.

Here, this rotation restricting configuration will be described.

As shown in FIG. 7, at the outer peripheral part of the restricting member 5, a plurality of (two in the present embodiment) ribs 56 is formed protrudedly. Each of ribs 56 is arranged at equal intervals along the circumferential direction of the outer peripheral part of the restricting member 5. In addition, each of ribs 56 extends along the center axis direction of the restricting member 5.

As shown in FIG. 8, at the inner peripheral part 722 of the operation member body 7 of the operation member 11, a groove 74, into which each of ribs 56 is inserted, is formed. Then, by inserting the rib 56 into the groove 74, the relative rotation between the restricting member 5 and the operation member 11 is better able to be restricted.

In addition, as shown in FIG. 7, at the inner peripheral part of the restricting member 5, a plurality of (two in the present embodiment) grooves 57 is formed. Each of grooves 57 is arranged at equal intervals along the circumferential direction of the inner peripheral part of the restricting member 5. In addition, each of grooves 57 extends along the center axis direction of the restricting member 5.

On the other hand, at the outer peripheral part 642 of the cover member body 61 of the cover member 6, a rib 67 inserted into each of grooves 57 is formed protrudedly. Then, by inserting the rib 67 into the groove 57, the relative rotation between the cover member 6 and the restricting member 5 is better able to be restricted.

Next, the usage of the liquid administration device 10 and the operation state when in use will be described with reference to FIGS. 1 to 6.

[1] The liquid administration device 10 in an unused state (initial state) as shown in FIGS. 1 and 4 is prepared. In the liquid administration device 10 in this unused state, the cover member 6 is in the first position and covers the tip side needle tip 21 of the double ended needle 2. In this unused state, the tip side needle tip 21 is maintained to be covered by the cover member 6 by the biasing force of the coil spring 60. As a result, erroneous puncturing by the tip side needle tip 21 can be better able to be prevented.

At this time, the restricting member 5 is in the first state, that is, each of first engagement parts 51 is engaged with each of first cover side engagement parts 65 of the cover member 6. As a result, the restricting member 5 has been made in a movable state with the cover member 6 (see FIG. 1).

In addition, in the puncture needle 50, the base end side needle tip 23 of the double ended needle 2 is separated from the sealing member 15 of the inner cylinder 1 of the cylindrical body 40, and not yet piercing the sealing member 15. As a result, the liquid Q can be maintained in an aseptic state until administration of the liquid Q starts.

In the restricting part 30, each of restricting parts 8 is positioned in the restricting position and is engaged with the base end 49 of the outer cylinder 4 of the cylindrical body 40. As a result, the operation (movement) of the operation member 11 to the base end direction for moving the gasket 3 is inhibited. Therefore, erroneous operation by the operation member 11 can be better able to be prevented.

[2] Next, the operation member body 7 of the operation member 11 of the liquid administration device 10 in the unused state is held. As shown in FIGS. 2 and 5, the tip wall part 63 of the cover member 6 is abutted to the living body B and the operation member 11 is pressed toward the tip direction in this state.

At this time, the cover member 6 moves from the first position to the second position against the biasing force of the coil spring 60. As a result, the tip side needle tip 21 of the double ended needle 2 protrudes from an opening part 631 of the tip wall part 63 of the cover member 6, and the living body B is punctured with the tip side needle tip 21.

In addition, in the moving process of the cover member 6, the tip wall part 63 of the cover member 6 presses the support member 9 of the puncture needle 50 toward the base end direction. As a result, the sealing member 15 of the inner cylinder 1 can be punctured with the base end side needle tip 23 of the double ended needle 2, and thus the double ended needle 2, which has punctured the living body B, is communicated with the inner cylinder 1.

Moreover, in the moving process of the cover member 6, the restriction release part 623 of the cover member 6 abuts on the engagement part 82 of each of restricting parts 8 of the restricting part 30 from its tip side, presses each of restricting parts 8 toward inside, and moves the restricting part 8 to the releasing position. As a result, the operation member 11 presses the gasket 3 and restriction on the pressing operation to discharge the liquid Q is released. Thus, the pressing operation is made possible. Thereafter, each of restricting parts 8 is pressed by the outer cylinder side tapered part 48 of the outer cylinder 4 and the inner cylinder side tapered part 131 of the inner cylinder 1 in order, and moves further to inside from the releasing position. As a result, the gasket 3 moves toward the tip direction, that is, the pressing operation is performed. Thus, the administration of the liquid Q can be performed. Then, this pressing operation is continued to be performed until the gasket 3 abuts on the bottom part 12 of the inner cylinder 1. As a result, the administration of the liquid Q is completed.

When the pressing operation by the operation member 11 is complete, the restricting member 5 is in the second state. That is, the restricting member 5 moves to the second position together with the cover member 6, while each of first engagement parts 51 is being engaged with each of first cover side engagement parts 65 of the cover member 6 (see FIG. 2). Then, in this position, each of second engagement parts 52 of the restricting member 5 is engaged with each of operation part side engagement parts 73 of the operation member 11 (see FIG. 5)

[3] Next, as shown in FIGS. 3 and 6, the liquid administration device 10 is separated from the living body B.

At this time, the cover member 6 moves from the second position to the third position by the biasing force of the coil spring 60. As a result, the tip side needle tip 21 of the double ended needle 2 is re-covered by the cover member 6, and thus the erroneous puncturing by the tip side needle tip 21 is better able to be prevented.

In addition, the restricting member 5 is in the third state.

In other words, each of second engagement parts 52 of the restricting member 5 has been maintained to be engaged with each of operation part side engagement parts 73 of the operation member 11 (see FIG. 6). As a result, the restricting member 5 is restricted to move to the third position together with the cover member 6. In addition, with the movement of the cover member 6, each of first engagement parts 51 of the restricting member 5 can go beyond each of first cover side engagement parts 65 of the cover member 6 by the inclined part 512 of the first protruded part 511, and as a result, is removed from the first cover side engagement part 65. Then, each of first engagement parts 51 removed from this first cover side engagement part 65 is engaged with each of second cover side engagement parts 66 of the cover member 6 (see FIG. 3). As a result, moving back of the cover member 6 to the second position is restricted, and the tip side needle tip 21 of the double ended needle 2 is maintained to be covered by the cover member 6. Therefore, the erroneous puncturing by the tip side needle tip 21 can be better able to be prevented after use of the liquid administration device 10, and the safety can be better able to be achieved.

In addition, in the liquid administration device 10, the pressing operation by the operation member 11 is inhibited until the puncturing into the living body B is complete. Therefore, it is possible to be able to better prevent the operation member 11 from operating erroneously. That is, it is possible to be better able to prevent the operation member 11 from being operated erroneously before puncturing or during puncturing.

In addition, in the liquid administration device 10, a series of operations from puncturing to administration can be accurately and better performed by a single action. The single action is holding the operation member 11 and straightly pressing the operation member 11 to the end.

Although the embodiments illustrated herein has been described above for the liquid administration device of the present invention, the present invention is not limited thereto. Each part configuring the liquid administration device can be replaced by one or more having differing structures from those described herein which can exhibit the equivalent function.

Further, in the above-described embodiments, the cylindrical body, in which the gasket slides inside, is configured by two members of the inner cylinder and the outer cylinder, it is not limited thereto. For example, the cylindrical body may be configured by one member.

Further, although in the above-described embodiments the puncture needle is the one having the needle tube being the double ended needle, the puncture needle is not limited thereto. The puncture needle may be the one having a needle tube without the base end side needle tip. In this case, the needle tube is preliminarily (already in the unused state) communicated with an inner cylinder.

In addition, in the above-described embodiment, the cover member, the restricting member, and the holding part are configured, so that the relative rotation is restricted by the engagement of the rib with the groove, it is not limited thereto. For example, the cover member, the restricting member, and the holding part may be configured to be formed in an elliptical-cylindrical shape or in a substantially rectangular-cylindrical shape, so that the relative rotation is restricted.

Generally speaking, a preferred arrangement for a commercial-sold liquid administration device incorporating the present invention can include: a cylindrically-shaped cylindrical body configured to be at least partially filled with liquid in its inside; a needle tube configured to be provided being communicated or communicable with the cylindrical body at the tip side of the cylindrical body, and to have a sharp needle tip at the tip; a gasket configured to be capable of sliding within the cylindrical body; an operation member configured to be provided at the base end side of the gasket and to perform pressing operation to discharge the liquid from the needle tube by pressing the gasket toward the tip direction; a cover member configured to be capable of moving to a first position, in which at least the needle tip of the needle tube is covered, to a second position, moved from the first position to the base end direction, in which the needle tip is exposed, and to a third position, moved from the second position to the tip direction, in which at least the needle tip is re-covered; and a restricting member configured to take a state where the cover member is allowed to move from the first position to the second position, and to take a state where moving back of the cover member to the second position is restricted after the cover member has moved from the second position to the third position. Therefore, it is possible to better able to ensure safety after use.

What is claimed is:

1. A liquid administration device comprising:
a cylindrical body configured to be at least partially filled with liquid;
a needle tube configured to communicate with or be communicable with the cylindrical body at the tip side of the cylindrical body, and having a sharp needle tip;
a gasket configured to slide within the cylindrical body;
a cylindrical operation member provided at a base end side of the gasket and configured to perform a pressing operation to discharge the liquid from the needle tube by pressing the gasket toward a tip direction, wherein an outer periphery of the operation member has a holding part configured to be held when the pressing operation is performed;
a cover member configured to move to:
a first position, in which at least the needle tip of the needle tube is covered,
a second position, in which the cover member has been moved in a base end direction from the first position, and in which the needle tip is exposed, and
a third position, in which the cover member has been moved in a tip direction from the second position, and in which at least the needle tip is re-covered; and
a restricting member configured to restrict movement of the cover member,
wherein the restricting member comprises a first engagement part and a second engagement part at different positions from each other,
wherein the cover member comprises:
a first cover side engagement part with which the first engagement part is configured to be engaged, and
a second cover side engagement part with which the first engagement part is configured to be engaged at different times from the first cover side engagement part, the second cover side engagement part being located at a base end side of the first cover side engagement part,
wherein the operation member comprises an operation part side engagement part with which the second engagement part is configured to be engaged,
wherein, when the cover member is in the first position, the restricting member takes a first state in which the first engagement part is engaged with the first cover side engagement part,
wherein, when the cover member has moved from the first position to the second position and the pressing operation by the operation member has been completed, the restricting member moves together with the cover member, while the first engagement part is engaged with the first cover side engagement part, and the restricting member takes a second state in which the second engagement part is engaged with the operation part side engagement part,
wherein, when the cover member moves from the second position to the third position, the first engagement part is removed from the first cover side engagement part and is engaged with the second cover side engagement part, while the second engagement part is engaged with the operation part side engagement part, and the restricting member takes a third state in which the cover member is restricted from moving back to the second position, and
wherein each of the cover member and the restricting member comprises a cylindrically-shaped member, and the cover member, the restricting member, and the holding part are arranged concentrically from inside to outside, in that order.

2. The liquid administration device according to claim 1, wherein relative rotation among the cover member, the restricting member, and the holding part is restricted.

3. The liquid administration device according to claim 1, wherein the first engagement part and the second engagement part are arranged in different positions along a center axis of the restricting member and also around the center axis of the restricting member.

4. The liquid administration device according to claim 1, wherein each of the first engagement part and the second engagement part is configured to deform elastically.

5. The liquid administration device according to claim 1, further comprising a biasing member configured to bias the cover member toward the tip direction.

6. The liquid administration device according to claim 1, further comprising:
a support member configured to movably support the needle tube relative to the cylindrical body along a center axis of the needle tube,
wherein the cylindrical body has a bottomed cylindrical shape, and has a cylinder main body having an opening part at its bottom through which the liquid passes, and a sealing part configured by an elastic material that seals the opening part in a liquid-tight manner,
wherein the needle tube comprises a double ended needle further having a sharp base end side needle tip and is communicable with the cylindrical body by piercing the sealing part with the base end side needle tip,
when the cover member is in the first position, the base end side needle tip is separated from the sealing part, and when the cover member moves to the second position, the cover member moves the needle tube with the support member toward the base end direction and the sealing part is pierced.

7. The liquid administration device according to claim 6, further comprising a fixing member located around an outer periphery of the sealing part.

8. The liquid administration device according to claim 7, wherein the fixing member is ring-shaped.

9. The liquid administration device according to claim 6, wherein the sealing part comprises a disk-shaped elastic piece.

10. The liquid administration device according to claim 9, wherein a ring-shaped recessed part is formed on a base end surface of the disk-shaped elastic piece.

11. A liquid administration device comprising:
a cylindrical body configured to be at least partially filled with liquid;
a needle tube configured to communicate with or be communicable with the cylindrical body at the tip side of the cylindrical body, and having a sharp needle tip;
a gasket configured to slide within the cylindrical body;
an operation member provided at a base end side of the gasket and configured to perform a pressing operation to discharge the liquid from the needle tube by pressing the gasket toward a tip direction, wherein an outer periphery of the operation member has a holding part configured to be held when the pressing operation is performed;
a cover member configured to move to:
a first position, in which at least the needle tip of the needle tube is covered,
a second position, in which the cover member has been moved in a base end direction from the first position, and in which the needle tip is exposed, and
a third position, in which the cover member has been moved in a tip direction from the second position, and in which at least the needle tip is re-covered; and
a restricting member configured to restrict movement of the cover member,
wherein the restricting member comprises a first engagement part and a second engagement part at different positions from each other,
wherein the cover member comprises:
a first cover side engagement part with which the first engagement part is configured to be engaged, and
a second cover side engagement part with which the first engagement part is configured to be engaged at different times from the first cover side engagement part, the second cover side engagement part being located at a base end side of the first cover side engagement part,
wherein the operation member comprises an operation part side engagement part with which the second engagement part is configured to be engaged,
wherein, when the cover member is in the first position, the restricting member takes a first state in which the first engagement part is engaged with the first cover side engagement part,
wherein, when the cover member has moved from the first position to the second position and the pressing operation by the operation member has been completed, the restricting member moves together with the cover member, while the first engagement part is engaged with the first cover side engagement part, and the restricting member takes a second state in which the second engagement part is engaged with the operation part side engagement part,
wherein, when the cover member moves from the second position to the third position, the first engagement part is removed from the first cover side engagement part and is engaged with the second cover side engagement part, while the second engagement part is engaged with the operation part side engagement part, and the restricting member takes a third state in which the cover member is restricted from moving back to the second position,
wherein, when the cover member is in the first position, at least a portion of the restricting member is located distally of a distal end of the operation member, and
wherein a distance between a proximal end of the operation member and a distal end of the restricting member is longer when the cover member is in the first position than when the cover member is in the second position.

12. The liquid administration device according to claim 11, wherein, when the cover member is in the second position, a distal end of the restricting member is located proximally of the distal end of the operation member.

13. The liquid administration device according to claim 11, wherein, when the cover member is in the third position, a distal end of the cover member is located distally of the distal end of the operation member, a proximal end of the cover member is located proximally of the distal end of the operation member, and a distal end of the restricting member is located proximally of the distal end of the operation member.

14. The liquid administration device according to claim 11, wherein, when the cover member is in the third position, the first cover side engagement part of the cover member is located distally of the distal end of the operation member, the second cover side engagement part of the cover member is located proximally of the distal end of the operation member, and a distal end of the restricting member is located proximally of the distal end of the operation member.

15. The liquid administration device according to claim 11, wherein the first cover side engagement part of the cover member and the second cover side engagement part of the cover member are arranged in a line in an axial direction of the cover member.

16. The liquid administration device according to claim 11, wherein the first engagement part and the second engagement part are at different positions in a circumferential direction.

17. A liquid administration device comprising:
- a cylindrical body configured to be at least partially filled with liquid;
- a needle tube configured to communicate with or be communicable with the cylindrical body at the tip side of the cylindrical body, and having a sharp needle tip;
- a gasket configured to slide within the cylindrical body;
- an operation member provided at a base end side of the gasket and configured to perform a pressing operation to discharge the liquid from the needle tube by pressing the gasket toward a tip direction, wherein an outer periphery of the operation member has a holding part configured to be held when the pressing operation is performed;
- a cover member configured to move to:
  - a first position, in which at least the needle tip of the needle tube is covered,
  - a second position, in which the cover member has been moved in a base end direction from the first position, and in which the needle tip is exposed, and
  - a third position, in which the cover member has been moved in a tip direction from the second position, and in which at least the needle tip is re-covered; and
- a restricting member configured to restrict movement of the cover member,
- wherein the restricting member comprises a first engagement part and a second engagement part at different positions from each other,
- wherein the cover member comprises:
  - a first cover side engagement part with which the first engagement part is configured to be engaged, and
  - a second cover side engagement part with which the first engagement part is configured to be engaged at different times from the first cover side engagement part, the second cover side engagement part being located at a base end side of the first cover side engagement part,
- wherein the operation member comprises an operation part side engagement part with which the second engagement part is configured to be engaged,
- wherein, when the cover member is in the first position, the restricting member takes a first state in which the first engagement part is engaged with the first cover side engagement part,
- wherein, when the cover member has moved from the first position to the second position and the pressing operation by the operation member has been completed, the restricting member moves together with the cover member, while the first engagement part is engaged with the first cover side engagement part, and the restricting member takes a second state in which the second engagement part is engaged with the operation part side engagement part,
- wherein, when the cover member moves from the second position to the third position, the first engagement part is removed from the first cover side engagement part and is engaged with the second cover side engagement part, while the second engagement part is engaged with the operation part side engagement part, and the restricting member takes a third state in which the cover member is restricted from moving back to the second position,
- wherein, when the cover member is in the first position, at least a portion of the restricting member is located distally of a distal end of the operation member, and
- wherein, when the cover member is in the third position, a distal end of the cover member is located distally of the distal end of the operation member, a proximal end of the cover member is located proximally of the distal end of the operation member, and a distal end of the restricting member is located proximally of the distal end of the operation member.

* * * * *